US011090248B2

(12) United States Patent
Finnen

(10) Patent No.: US 11,090,248 B2
(45) Date of Patent: Aug. 17, 2021

(54) COMPOUNDS AND COMPOSITIONS FOR USE

(71) Applicant: DR WELLER LIMITED, Southampton (GB)

(72) Inventor: Mike Finnen, Edinburgh (GB)

(73) Assignee: DR WELLER LIMITED, Southampton (GB)

( * ) Notice: Subject to any disclaimer, the term of this patent is extended or adjusted under 35 U.S.C. 154(b) by 0 days.

(21) Appl. No.: 16/329,945

(22) PCT Filed: Sep. 1, 2017

(86) PCT No.: PCT/GB2017/052551
§ 371 (c)(1),
(2) Date: Mar. 1, 2019

(87) PCT Pub. No.: WO2018/042189
PCT Pub. Date: Mar. 8, 2018

(65) Prior Publication Data
US 2019/0183770 A1 Jun. 20, 2019

(30) Foreign Application Priority Data
Sep. 2, 2016 (GB) ..................... 1614961

(51) Int. Cl.
| | | |
|---|---|---|
| *A61K 8/63* | (2006.01) | |
| *A61K 8/44* | (2006.01) | |
| *A61K 8/49* | (2006.01) | |
| *A61K 8/64* | (2006.01) | |
| *A61Q 17/04* | (2006.01) | |
| *A61K 8/19* | (2006.01) | |
| *A61K 8/46* | (2006.01) | |
| *A61Q 19/00* | (2006.01) | |
| *A61K 8/36* | (2006.01) | |

(52) U.S. Cl.
CPC .............. *A61K 8/63* (2013.01); *A61K 8/19* (2013.01); *A61K 8/36* (2013.01); *A61K 8/361* (2013.01); *A61K 8/447* (2013.01); *A61K 8/46* (2013.01); *A61K 8/4986* (2013.01); *A61K 8/64* (2013.01); *A61Q 17/04* (2013.01); *A61Q 19/00* (2013.01); *A61K 2800/592* (2013.01)

(58) Field of Classification Search
CPC ........ A61K 8/63; A61K 8/447; A61K 8/4986; A61K 8/64; A61K 8/19; A61K 8/46; A61K 8/36; A61K 2800/592; A61Q 17/04; A61Q 19/00
See application file for complete search history.

(56) References Cited

U.S. PATENT DOCUMENTS

| | | | | |
|---|---|---|---|---|
| 5,545,402 | A | * | 8/1996 | Watkinson ............... A61K 8/66 424/94.63 |
| 9,283,550 | B2 | | 3/2016 | Morris et al. |
| 2002/0172702 | A1 | * | 11/2002 | Bekele .................... A61Q 1/06 424/401 |
| 2003/0068297 | A1 | | 4/2003 | Jain |
| 2007/0299410 | A1 | * | 12/2007 | Eknoian ............... A61K 8/0208 604/289 |
| 2010/0093984 | A1 | | 4/2010 | Wirth et al. |
| 2012/0156163 | A1 | | 6/2012 | Bauman et al. |
| 2013/0149271 | A1 | | 6/2013 | Van Gogh |

FOREIGN PATENT DOCUMENTS

| | | |
|---|---|---|
| EP | 1145707 | 10/2001 |
| FR | 2883177 | 9/2006 |
| WO | 2003/017989 | 3/2003 |
| WO | 2006/095193 | 9/2006 |
| WO | 2012/153331 | 11/2012 |

OTHER PUBLICATIONS

International Search Report and Written Opinion corresponding to International Application No. PCT/GB2017/052551 dated Mar. 1, 2018, 29 pages.
European Examination Report corresponding to EP 17783951.1; dated Jul. 29, 2020 (10 pages).
Mintel Product Description for "Anti-Aging Face Sunscreen SPF 30" Record ID: 2030291, published Apr. 2013 (5 pages).
Mintel Product Description for "Anti-Aging Eye Contour Sunscreen SPF 30" Record ID: 2030316, published Jun. 2013 (5 pages).

\* cited by examiner

*Primary Examiner* — Shirley V Gembeh
(74) *Attorney, Agent, or Firm* — Myers Bigel, P.A

(57) ABSTRACT

The present disclosure provides compositions which may be used to augment, supplement and/or replace the products of certain UV sensitive/dependent processes. In particular, the disclosure provides sunscreen compositions which avoid problems associated with prior art sunscreen compositions which inhibit the natural progression of certain in vivo sunlight/UV dependent processes including processes which result in Nitric Oxide/Vitamin D production in the skin.

5 Claims, 8 Drawing Sheets

EFFECTIVE

-SH

Glutathione

Thiolactate

S-S

Dithioglycolate

Lipoic acid

Cystine

COMPOUNDS AND COMPOSITIONS FOR USE

FIELD

Figure 1:
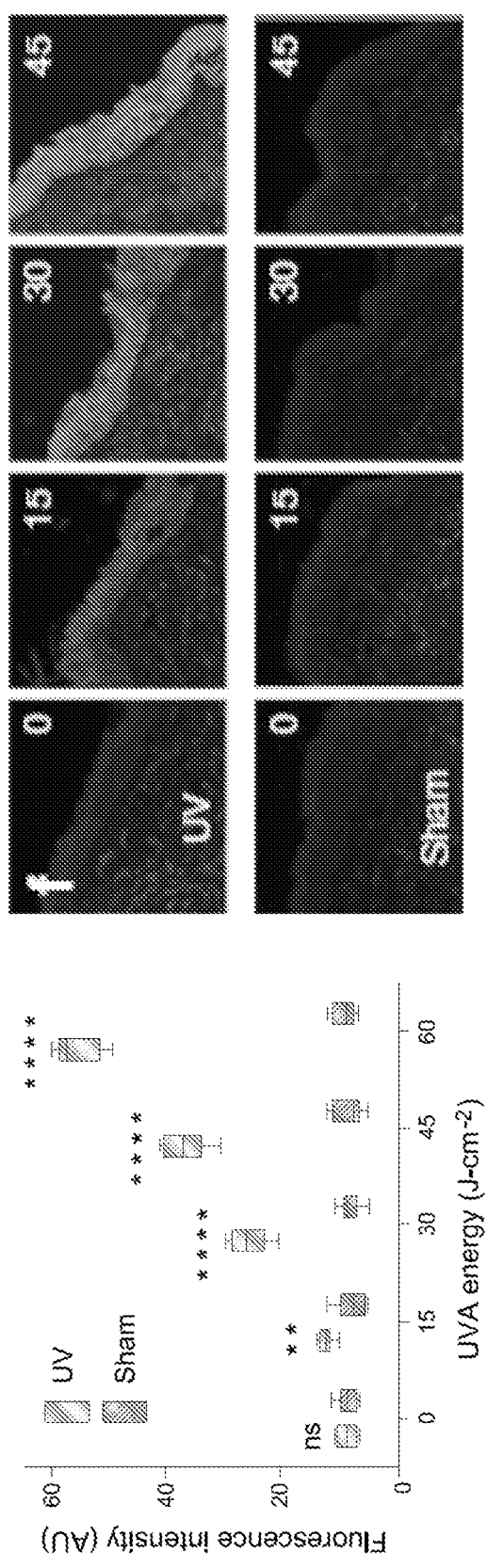

The present disclosure provides compounds and compositions which may be used to augment, supplement and/or replace the products of certain UV sensitive/dependent processes.

BACKGROUND

The benefits and/or dangers of exposure to the sun are continually debated. On the one hand people are afraid of sun exposure as too much exposure carries a risk of skin damage (sun burn/blistering), skin cancer and acceleration of the aging process. Other people are more relaxed about exposure to the sun and will recite numerous health benefits that include the production of vitamin D.

Vitamin D production is important and a recent Public Health England communication recommended that people take supplements at least between October and March in order to ensure that they receive enough vitamin D. In a study conducted at the University of California, San Diego, researchers combined data from satellite measurements of sunlight and cloud during the winter to estimate the serum level of vitamin D metabolite of people living in 177 countries. The data revealed a link between low vitamin D levels and an increased risk of colorectal and breast cancer. According to the researchers, raising the serum levels of vitamin D and/or its metabolite was found to be ideal for cancer prevention. Thus with sufficient exposure to sunlight, there is the potential for 600,000 cases of breast and colorectal cancer to be prevented each year.

The amount of daylight a subject is exposed to is also vital to maintaining a normal circadian rhythm. These rhythms include physical, mental, and behavioural changes that follow a 24-hour cycle and respond to light and darkness in the body's environment. The sleep-wake cycle is contingent on morning sunlight to help you sleep at night. Natural daylight helps your body clock restart to its active daytime phase. To ensure that your body clock is in sync, the advice is to go outside and get some sunlight when you wake up Regular sunlight exposure can naturally increase the serotonin levels in your body, making you more active and alert. Indeed exposure to bright light is seen as an approach to increase serotonin without the use of drugs. There is a positive correlation between the development of serotonin and the hours of sunlight during the day and in a sample of 101 healthy men, it was found that the turnover of serotonin in the brain was lowest during the winter whereas the production rate of serotonin was highest when the subjects stayed in the sunlight longer. Thus spending more time in the sun can help people avoid what is commonly referred to as the "winter blues".

Seasonal affective disorder (SAD), seasonal depression, and mood variation have also been linked to sunlight exposure. As stated, blood levels of vitamin D3, are relatively low in the winter months and exposure to sunlight can equip your body to stock up on vitamin D3 that can last as a reserve during the winter months.

Skin that is exposed to ultraviolet (UV) rays releases a compound, nitric oxide, that lowers blood pressure. In a recent study conducted at Edinburgh University, dermatologists studied the blood pressure of 34 volunteers under UV and heat lamps. In one session, the volunteers were exposed to both light sources and in the other session, the UV rays were blocked so only the heat affected the skin. The results of the study showed a significant drop in blood pressure after exposure to UV rays for an hour but not after the heat-only sessions. It is important to note that the volunteers' vitamin D levels were unaffected in both sessions.

It has also been suggested that, safe sun exposure can actually protect you from melanoma. The skin's exposure to ultraviolet radiation of short wavelengths (UVB) has been linked to a decreased risk of melanoma in outdoor workers compared to their indoor counterparts, which suggests chronic sunlight exposure can have a protective effect, says The Lancet Journal. In a study, indoor workers were found to have increased rates of melanoma because they were only exposed to UVA light, which is associated with skin damage and skin cancer. These workers were found to get three to nine times less solar UV exposure than outdoor workers and therefore had lower levels of vitamin D. It was reported that indoors, UV breaks down vitamin D3 formed after outdoor UVB exposure, which can result in a vitamin D deficiency and increase the risk of melanoma.

The most notable benefit of exposure to sunlight is its ability to boost your body's vitamin D supply. The NIH says at least 1,000 different genes that control every tissue in the body are linked to be regulated by vitamin D3. Vitamin D is produced by the skin's response to UV radiation primarily through sun exposure, which affects 10 percent of the genes in the human body. In a study, researchers did vitamin D screenings on approximately 500 children admitted to a pediatric hospital ward for 12 months. Two in five children were found to have a vitamin D deficiency, which was linked to severe illness and a longer hospital stay. A healthy supply of vitamin D promotes bone growth and prevent illnesses such as breast and colon cancer, inflammation, multiple sclerosis, seasonal disorders, and depression.

SUMMARY

There are numerous benefits that are thought to be associated with exposure to sunlight. For example, exposure to sunlight promotes the production of vitamin D (an important factor in preventing bone deformities (such as rickets) and certain types of cancer). Other benefits include the positive effect of sunlight on blood pressure (alleviating hypertension) and a person's mood/wellbeing.

Without wishing to be bound by theory, it is suggested that at least some of the benefits associated with sunlight exposure require or result in nitric oxide (NO) production in the skin. Nitric Oxide production in the skin has a number of therapeutic advantages; for example, it plays an important role in cellular signalling and is involved in many different processes. One of its key roles is as a short-lived but powerful vasodilator and it will be appreciate that this can have a direct and positive effect on blood pressure.

Mechanisms which lead to the production of NO in the skin following exposure to sunlight (or at least the UV component thereof) are known. Specifically, it is hypothesised that UVA induced decomposition of nitrite ($NO_2^-$; see equations 1-5 in Table 2) is self-limiting due to reaction with $NO_2$. (see equation 4 in Table 2). However, in the presence of reduced thiols such as reduced glutathione, nitrosothiols are formed which then decompose on UVA challenge producing high levels of NO (equations 6-9 in Table 2).

Other benefits associated with exposure to sunlight include, for example, the production of vitamin D in the skin. UV light (especially UV-B light) from the sun physically induces the formation of pre-Vitamin D3 in the skin from 7-dehydro cholesterol, a compound which is naturally present in the skin. This then undergoes thermal re-arrangement to form Vitamin D3 which then diffuses from the skin to the circulation where it is eventually 25-hydroxylated in the liver and 1-hydroxylated in the kidney to generate active Vitamin D. It should be noted that NO may have positive effects on these hydroxylating enzymes.

Nevertheless, there is widespread concern that any degree or level of exposure to sunlight (and in particular the UV components thereof) is detrimental, leading to skin damage (often manifesting as sun-burn and/or blistering) and in extreme cases, certain types of cancer. As such people are advised to use sunscreen or sun-blocking compositions to protect their skin from the harmful effects of the sun.

It should be understood that throughout this specification, the terms "comprise", "comprising" and/or "comprises" is/are used to denote that aspects and embodiments of this invention "comprise" a particular feature or features. It should be understood that this/these terms may also encompass aspects and/or embodiments which "consist essentially of" or "consist of" the relevant feature or features.

For convenience, the term "sunscreen" will be used hereinafter but it should be understood that this term embraces compositions which are for topical application to the skin (or hair/nails), in particular those areas which are sun-exposed, especially the skin of humans. Sunscreen compositions can be in the form of a liquid, lotion, cream, ointment, oil, foam, scrub, gel, toner and the like. The term "sunscreen" or "sunscreen composition" may embrace both organic type compositions (namely those compositions which comprise "organic" compounds which provide protection from exposure to the sun) and inorganic type compositions (in which compounds such as titanium dioxide and/or zinc oxide are used to provide protection from the effects of sun exposure). The term "sunscreen composition" may include any composition used to protect the skin from exposure to sunlight (and/or the UV component thereof) and will include those compositions referred to as, for example, "masks", "sunblock", "suntan lotion", "sun cream" and certain types of "after sun". The term "sunscreen" may also embrace certain cosmetic and/or beauty products (including make-up) which, when applied to the skin has a UV or sunlight protecting effect. Indeed, the term "sunscreen" may be applied to any product with an SPF rating. In addition to those non-limiting examples already mentioned, other non-limiting examples may include antiperspirants, deodorants, lipsticks, chap-sticks, foundations, mascara, sunless tanners and fake-tan compositions.

Sunscreen compositions may contain one or more active ingredients designed and/or selected to reduce the level of skin exposure to sunlight and/or the UV (UVA/UVB) components thereof. The active components may take the form of organic/inorganic chemicals/particulates. Some sunscreens may contain a plurality of different active components including, for example, combinations of different organic/inorganic particulates/chemicals. Suitable active components will be known to one of skill in this field but an organic chemical active component may comprise a compound that absorbs UV light. An inorganic particulate active component may comprise a compound or moiety that reflects, scatters and/or absorbs light (including UV light). For example, silica, fumed silica, iron oxide, titanium dioxide and/or zinc oxide may be used. Active organic particulates may include those that absorb light (light the subset of useful organic chemicals) but which also contain multiple chromophores that (like the useful inorganic particulates) reflect and scatter a fraction of light. Tinosorb M is an example of a suitable organic particulate for use as an active component of a sunscreen composition. Thus sunscreen compositions contain one or more active components, which active components are, when in use (and applied to the skin) designed to reduce (by, for example, light absorption and/or light reflecting/scattering based mechanisms) the exposure of skin to sunlight.

As stated, compositions which may be regarded as sunscreen type compositions are provided in (or with) a variety of SPF ratings. The SPF rating is a measure of the fraction of sunburn-producing UV sunlight rays which reach the skin. The higher the SPF rating, the fewer rays reach the skin. Thus, a sunscreen with an SPF rating of 15 will allow more of the sun's UV rays to reach the skin than a sunscreen which is SPF rated 50.

However, while these compositions shield the skin from harmful sun rays and offer protection against the damaging, aging and cancer inducing effects thereof, they have an adverse effect on certain in vivo processes. Indeed, by reducing the amount of sunlight and/or any UV component thereof from reaching the skin, those in vivo processes which are UV or sunlight dependent, are blocked, inhibited and/or prevented from progressing. These in vivo processes (namely those processes which are dependent on sunlight/UV light exposure) may otherwise be referred to as "photosensitive processes". While one must carefully regulate one's exposure to sunlight, there are, as stated, advantages associated with exposure to sunlight and these advantages directly or indirectly stem from the progression of one or more in vivo sunlight/UV dependent (photosensitive) processes. These processes may occur in the skin and may generate metabolites, intermediates and/or products which are useful in other processes and/or which have a therapeutic or health promoting effect.

It should be understood that the phrase "in vivo sunlight/UV dependent (photosensitive) processes" may include those processes which generate (either directly or indirectly via certain intermediates and/or metabolites) vitamin D and/or NO in the skin.

When applied to the skin, a sunscreen composition of the type described herein prevents the skin from becoming exposed (or over exposed) to sunlight and/or the UV component thereof. As such, the application of a sunscreen (blocking exposure of the skin to UV light) has a negative (inhibiting) effect on one or more of the aforementioned in vivo sunlight/UV dependent processes.

As explained above, it is suggested that many of the benefits associated with exposure to sunlight occur as a consequence of the resulting nitric oxide production in the skin. The skin-based production of nitric oxide is, in part, dependent upon a mechanism which requires exposure to UV light (see above and the information presented in Table 1) and therefore, using a sunscreen composition to block or prevent exposure of the skin to UV light, inhibits the progression of any sunlight/UV dependent process for the generation of NO. This in turn will reduce the therapeutic effects associated with NO production, including, for example local (skin-based) NO production.

The present disclosure is based on the finding that although sunscreen compositions can (when in use and applied to the skin) inhibit the natural progression of certain in vivo sunlight/UV dependent processes (including processes which result in NO/Vit D production in the skin), this effect can be countered or offset by the use of other compounds which:

replicate these in vivo sunlight/UV dependent processes;
provide or generate suitable intermediates or metabolites for use in these in vivo sunlight/UV dependent processes; and/or
provide or generate the products of these in vivo sunlight/UV dependent processes.

Thus, the present disclosure provides sunscreens which avoid the problem of prior art sunscreens which prevent the natural delivery of NO and Vitamin D3 via sunlight exposure.

Where these other compounds (as noted above) provide intermediates or metabolites for use in in vivo sunlight/UV dependent processes, they may replace those intermediates and/or metabolites which are lost through the UV blocking effect of a sunscreen composition. In such circumstances, the in vivo process which would normally be dependent upon products generated following exposure to sunlight, can proceed using the metabolites and/or intermediates generated by the "other compounds" mentioned above.

By way of example, this disclosure relates to compounds which can generate NO or pre-vitamin D3 (which may then be used by the body to generate useful or active vitamin D), vitamin D3 and/or vitamin D upon exposure to UV light. These compounds may be used to supplement or replace natural or endogenously produced vitamin D/NO—especially skin-based vitamin D/NO, which natural or endogenous (skin-based) vitamin D/NO may be lost or reduced because of, for example, the use of a sunscreen composition which blocks sunlight/UV light exposure and which in turn inhibits those natural in vivo sunlight/UV dependent processes which would otherwise have generated endogenous (skin-based) vitamin D/NO.

Further, it has been surprisingly found that these compounds and/or metabolites, products and/or intermediates generated therefrom, are available for absorption into the skin—even when added to other compositions, including for example, sunscreen compositions. Without wishing to be bound by theory, it is suggested that the increased concentration gradient of these compounds (or any products, metabolites and/or intermediates generated (for example via exposure to UV/sunlight) therefrom) at the stratum corneum enhances diffusion through to the epidermis.

Thus this disclosure relates to 7-dehydrocholesterol and/or any precursor for vitamin D which, upon exposure to sunlight (or the UV component thereof), generates an intermediate or metabolite which can be used to generate active vitamin D in vivo. As explained in more detail below, such compounds may be added to sunscreen compositions to negate the inhibitory effect of the sunscreen on the body's natural vitamin D generation pathway.

The disclosure further provides thiol and/or disulfide compounds which, upon exposure to ultra violet (UV) radiation, react with nitrogen containing precursors of nitric oxide (NO-precursor) to generate long-lived nitric oxide adducts.

Without wishing to be bound by theory when any of the thiol and/or disulphide compositions described herein are exposed to radiation (such as UV radiation) and in the presence of an NO-precursor compound they form a nitrosothiol. The nitrosothiol may be bound to skin proteins and subsequently decompose (thermally or on further exposure to light) to deliver/produce a nitric oxide radical (NO.).

This disclosure identifies a cohort of useful thiol and disulfide compounds which, when exposed to UV radiation in the presence of an NO-precursor compound, deliver NO.. Indeed, the cohort of compounds has been found to provide a sustained generation of NO. from a nitrite source when exposed to UV radiation.

As stated (and without wishing to be bound by theory), the mechanism of UV-induced NO generation is illustrated by equations 1 to 5 in Table 2. Specifically, it is thought that UVA induced decomposition of nitrite ($NO_2^-$) is self-limiting due to reaction with $NO_2$. (see, for example, equation 4 in FIG. 1). However, in the presence of reduced thiols (e.g. reduced glutathione, denoted as GS in Table 2), nitrosothiols may be formed (see, for example equation 6, Table 2). The nitrosothiols may then undergo photolytic degradation to produce high levels of NO. (see equations 6-9 in Table 2).

It is further suggested (and again, without being bound by theory) that when the thiol or disulfide compounds described herein are exposed to radiation (such as UV radiation), they undergo homolytic cleavage to form a thiyl radical (RS.). The newly-formed thiyl radical may trap NO. to form a nitrosothiol. Subsequently, the nitrosothiol may be photolytically cleaved to release NO. and regenerate the thiyl radical.

As stated, the generation of NO from the thiol or disulfide compounds described herein takes place following exposure to UV and in the presence of an NO-precursor. As such, when in use (and as further described below), the thiol and/or disulfide compounds may be combined with a suitable NO-precursor compound.

The inventors hypothesise that the capacity of the thiol and/or disulfide compounds described herein to generate NO. in response to UV radiation may be influenced by a number of factors including, for example:

(i) the propensity of a thiol or disulfide compound to form the thiyl radical (RS.) when exposed to UV irradiation; and (ii) the relative stability of the formed nitrosothiol to photolytic cleavage.

Thiol ionization may be understood to strongly influence the reactivity of the thiol group (e.g. the S—H bond of thiols dissociates with pKa approximately in the range 7-10). However, the formation of a thiyl radical is generally the result of a one-electron oxidation of thiols. For instance, in the processes described herein, the thiyl radical may be formed via a photolytic cleavage of a —S—H or —S—S— bond. In contrast to the chemical reactivity of the thiol group, the inventors hypothesise that the response of thiols to UV radiation may be highly dependent on the groups adjacent to the thiol moiety.

Similarly, it is hypothesised that the ability of disulfide bonds to form a thiyl radical (RS.) or dithiyl radical via a photolytic rupture of a disulfide (S—S) bond may be highly dependent on the individual chemical structures involved. It will be appreciated that a dithiyl radical may be generated after homolytic cleavage of a disulfide bond contained within a cyclic structure.

Thus, the ability of any given thiol (RSH) and/or disulfide (RS—SR) compound to initiate a sustained NO generation process may depend on the individual chemical structures and groups present on the compound.

As such, the thiol or sulphide compounds described herein may comprise any compound capable of forming a photolytically cleavable nitrosothiol compound.

As used herein, the term photolytic cleavage may mean the homolytic rupture of a covalent bond to form two radical species upon exposure to radiation (e.g. UV radiation). This term may be used interchangeably with the terms photolysis and photolytic degradation.

Further, the term thiol represents a compound comprising an —S—H moiety.

The term disulfide represents a compound comprising a —S—S— moiety, including persulfides (R—SSH). As will be appreciated, a disulfide compound may be considered as an oxidised form of a thiol compound. In addition, the various embodiments (methods, compositions, medicaments and the like) described herein may exploit a thiol compound in a reduced form (e.g. the thiolate anion, RS⁻).

The thiol or disulfide compound may be an organic compound comprising an —SH or —S—S— moiety respectively and also including persulfides (R—SSH).

As used herein, an organic compound is a carbon-containing species that may optionally contain one or more heteroatoms such as N, O, S and/or P.

Accordingly, the thiol compound may be represented as:
(i) R—SH
(ii) the disulfide compound may be represented as R—S—S—R' (where R and R' may be identical groups or may be different).
(iii) the thiol compounds for use may comprise the following general formula:

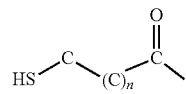

wherein n=6
(iv) the disulphide compounds for use may comprise the following general formula:

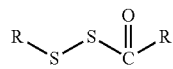

R and R' may each independently be a $C_1$-$C_{20}$, a $C_1$-$C_{15}$, a $C_1$-$C_{10}$, or a $C_1$-$C_5$ alkyl group. These alkyl groups contain from 1 to 20, 1 to 15, 1 to 10 or from 1 to 5 carbon atoms respectively. As used herein, an alkyl group is selected from a straight or branched chain hydrocarbon containing the defined number of carbon atoms.

Alternatively, R and R' together may form a cyclic structure. For example, they may together form a 5-, 6- or 7-membered ring. The cyclic structure may optionally be substituted with one or more alkyl groups (as defined for R and R' above).

The alkyl group may comprise substituents, optionally containing heteroatoms. For example, the alkyl group may be substituted with one or more carboxylic acid (—CO₂H), hydroxy (—OH) and/or amino (—NH₂) groups.

Optionally, one or more of the carbon atoms in the backbone of the alkyl chain may be replaced by a heteroatom containing functional group. For example, the alkyl chain may comprise one or more carbonyl, amide and/or ester groups. By way of further example, the alkyl chain may comprise a carbonyl group, such as a ketone. In some cases, the disulfide compound may be represented as

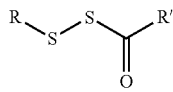

wherein R and R' are as defined above.

Representative examples of the thiol compounds used in the compositions of the invention include, but are not limited to, glutathione, cysteine, homocysteine, cysteamine, and thiolactate. Whilst a particularly useful stereoisomer of glutathione has been illustrated below, it will be appreciated that other stereoisomers of glutathione (and any other thiol compounds—including those mentioned above) and/or, for example salts and derivatives thereof, may also be used in the methods and compositions of the invention.

It should be noted that all salts, derivatives and/or sterioisomers should be functional—that is to say that they are capable of generating NO. in response to exposure to UV radiation (for example, in the presence of an NO-precursor compound).

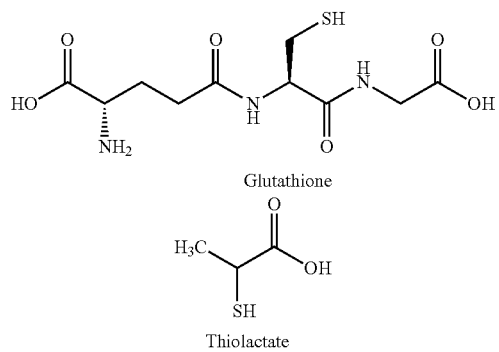

In addition, certain disulfide compounds were unexpectedly able to facilitate sustained NO. generation when exposed to UV radiation in the presence of an NO-precursor compound. Representative examples of the disulfide compounds include, but are not limited to, dithioglycolate, lipoic acid (oxidised) and cystine Again, whilst a particularly useful stereoisomer of cystine has been illustrated below, it will be appreciated that other stereoisomers of cystine (and the other disulfide compounds) may also be used in the methods and compositions of the invention.

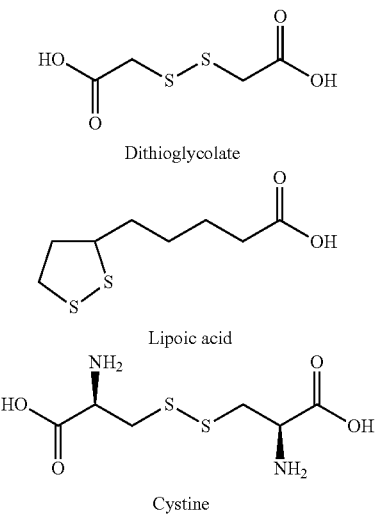

As used herein, a nitrogen containing precursors of nitric oxide (NO-precursor compound) may be any species capable of reacting with the thiol or disulfide compound to generate a photolytically cleavable nitrosothiol compound.

One or more NO-precursor compounds may be used together with any of the thiol and/or disulfide compounds described herein.

NO-precursor compounds may be selected from nitrite-containing compounds, nitrate-containing compounds and nitro-containing organic compounds.

For example, metal nitrites may be used as the NO-precursor compounds. Sodium nitrite (NaNO$_2$) is an example of one such NO-precursor compound. Other representative examples include, but are not limited to, potassium nitrite, dinitrosyl-iron complexes and other iron sulfur compounds etc.

In other cases, nitrate-containing compounds may be used. Representative examples include, but are not limited to, sodium nitrate, potassium nitrate etc.

Additionally, or alternatively, the NO-precursor compound may be a nitro-containing organic group. For example, the NO-precursor compound may be a carboxylic acid comprising a nitro (—NO$_2$) group. Representative examples include, but are not limited to, nitropropionic acid and/or nitrooleate. For example, the NO-precursor compound may be 3-nitropropionic acid, 9-nitrooleate or 10-nitrooleate.

The present disclosure also provides compositions comprising any one or more of the compound(s) described herein. For example, the disclosure provides compositions which comprise at least one of:

(1) a compound which upon exposure to sunlight (or the UV component thereof), generates NO or an intermediate or metabolite which can be used to generate NO in vivo;
(2) a thiol compound;
(3) a disulfide;
(4) a compound which upon exposure to sunlight (or the UV component thereof), generates vitamin D or an intermediate or metabolite which can be used to generate active vitamin D in vivo; and (5) 7-dehydrocholesterol Note, compounds (4) and (5) may hereinafter be referred to as "vitamin D generating compounds".

Any of the compositions described herein (including any of the sunscreen compositions) may be supplemented with one or more compounds comprising thiol and/or disulfide compounds selected from the group consisting of:

(i) Glutathione (GSH);
(ii) cysteine (CYS);
(iii) sodium nitrite (NO2);
(iv) sodium nitrate (NO3); and
(v) Lipoic acid (LA).

Alternatively or additionally, such (sunscreen) compositions may comprise 7-dehydrocholesterol (DHC).

Useful (NO generating) compounds may include, those comprising, for example NO$_2$GSH, NO$_3$GSH, NO$_2$CYS, NO2LA and/or NO$_3$LA. Sunscreen compositions of this disclosure may be supplemented with one or more of these NO generating components. Optionally, any one of these components may be used together with DHC (7-DHC) in a sunscreen composition.

Compositions of this invention may be formulated for topical administration (that is application to the skin). The compositions may be provided in the form of creams, liquids, ointments, oils and the like.

The compositions, particularly those comprising any of compounds (1)-(3) above, may optionally further comprise an NO-precursor compound as described herein.

The composition may be a sunscreen type composition.

A sunscreen composition according to this disclosure may be a sunscreen composition which facilitates the generation of NO and/or Vitamin D(3) is the skin of a user. This represents a Thus this disclosure provides sunscreen compositions which comprise (a) a thiol or disulfide compound; and (b) an NO-precursor compound.

The thiol, disulfide and/or NO-precursor compound(s) for use in a composition, for example a sunscreen composition, of this disclosure may be any one or more of those thiol, disulfide and/or NO-precursor compound(s) described herein.

The disclosure further provides sunscreen compositions which comprise 7-dehydrocholesterol.

As stated sunscreen compositions that are applied to the skin, act to prevent the skin from becoming exposed or over-exposed to sunlight and/or the UV component thereof. A consequence of this is that in vivo processes which require or depend on sun/UV light exposure are inhibit or prevented from progressing. Insofar as these processes lead to the generation of vitamin D or NO, this problem is avoided through the use of sunscreen compounds which are supplemented with at least a thiol and/or disulfide compound described herein and/or compounds which upon exposure to sunlight (or the UV component thereof), generates vitamin D or an intermediate or metabolite which can be used to generate active vitamin D in vivo.

The problem may further be solved by the use of sunscreen compositions that are yet further supplemented with NO-precursor compound(s)—again as described herein.

Without wishing to be bound by theory, upon exposure to ultra-violet (UV) radiation a thiol or disulfide compound and an NO-precursor compound in a supplemented sunscreen composition of this disclosure react together to form a nitrosothiol which decomposes to deliver a nitric oxide radical. It will be appreciated that at the initiation of the reaction, trace levels of NO. may already be present in the composition and be available to react with the newly-formed thiyl radicals. For instance, trace levels of NO. may be formed from the NO-precursor compound, e.g. a nitrite compound.

Further, and again without wishing to be bound by theory, any 7-dehydrocholesterol in a sunscreen composition, will, upon exposure to ultra-violet (UV) radiation (in particular UV-B radiation) generate pre-vitamin D3 in the skin. This then undergoes thermal re-arrangement to form Vitamin D3. The Vitamin D3 then diffuses from the skin to the circulation where it is 25-hydroxylated in the liver and 1-hydroxylated in the kidney thereby generating active Vitamin D.

A (sunscreen) composition of this disclosure may further include one or more facilitators and/or excipients. A facilitator may be added to the composition in order to expedite, for example, NO generation. Useful facilitators may act to prolong the half-life of the nitric oxide generated or to propagate the generation of nitric oxide in the system. Facilitators may also support the diffusion of generated compounds and intermediates to their site of action. Representative examples of a facilitator include, but are not limited to ascorbate, ceramide, erucic acid and homocysteine. As such, facilitators may be added to compositions comprising compounds which upon exposure to sunlight (or the UV component thereof), generate NO or an intermediate or metabolite which can be used to generate NO in vivo; a thiol compound and/or a disulfide compound.

The thiol, disulfide and/or vitamin D generating compounds provided by this disclosure may be formulated as supplements to be added to or used together with, an off-the-shelf (commercially available) sunscreen composition. For example, thiol and/or disulfide compounds for addition to sunscreen compositions may be purchased separately and mixed with or added to sunscreen compositions prior to application to the skin. A sunscreen composition to which a thiol and/or disulfide compound has been added may be referred to as a "supplemented" or "modified" sunscreen composition. As such, once a thiol and/or disulfide compound has been added to a sunscreen composition, the modified sunscreen may be applied in the usual manner to those areas of the skin that are to be protected from exposure to the sun.

Alternatively, the thiol and/or disulfide compounds may be formulated as compositions for topical application. Compositions comprising one or more thiol and/or disulfide compounds may be applied to the skin before, during and/or after any necessary sunscreen has been applied.

One of skill will appreciate that compositions comprising one or more thiol and/or disulfide compounds may be used to boost, augment or supplement NO production in the skin upon exposure to sunlight. As such, composition which comprise, consist essentially of or consist of any one or more of the thiol and/or disulfide compounds described herein may be applied to the skin without the need to apply a sunscreen composition too.

As such, the present disclosure provides:
(i) A composition comprising (or consisting essentially of, or consisting of) one or more of the thiol compounds described herein and/or one or more of the disulfide compounds described herein; and
(ii) A sunscreen composition comprising (or consisting essentially of, or consisting of) one or more of the thiol compounds and/or one or more the disulphide compounds described herein.

Compositions (i) and/or (ii) above may further comprise an NO-precursor compound as described herein and one or more suitable facilitators and/or excipients of this disclosure.

The sunscreen (and other) compositions of this invention may be formulated together with pharmaceutically, therapeutically and/or cosmetically acceptable diluents, excipients, carriers and the like. For example, a composition according to the present disclosure may be prepared conventionally, comprising substances that are customarily used in, for example, pharmaceutical compositions and as described in, for example, Remington's The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

For example, the compositions may be formulated with suitable stabilizers, wetting agents, emulsifiers, salts (for use in influencing osmotic pressure), buffers and/or other substances that do not react deleteriously with the active compounds. The compositions may comprise diluents other than water including, for example, liquid or solid emollients, solvents, humectants, thickeners and powders.

A composition of the disclosure may comprise or further comprise cosmetically acceptable excipients and/or bases. Suitable excipients and./or bases may have a cream, lotion, gel or emulsion format. Suitable bases may include creams commonly known as "vanishing creams" and which comprise an amount of fatty acid (for example 3 to 25%, more preferably 5 to 20% fatty acid) and optionally "soaps" (which may include alkali metal salts of fatty acids, like sodium or potassium salts) and water.

As stated, where the composition is a sunscreen composition, the composition may include one or more of the known and conventionally used sunscreen active agents (those light absorbing and/or reflecting moieties).

The disclosure further provides a kit, said kit comprising one or more thiol and/or disulfide compound(s) of this disclosure and/or a compound which upon exposure to sunlight (or the UV component thereof), generates vitamin D or an intermediate or metabolite which can be used to generate active vitamin D in vivo and/or 7-dehydrocholesterol. These various compound(s) may be provided in the form of compositions formulated for topical application and/or for addition to existing sunscreen compositions. The kit may comprise a composition which comprises both a thiol and a disulphide compound. The kit may further comprise an NO-precursor compound as described herein and one or more suitable facilitators and/or excipients of this disclosure. Any NO-precursor compound(s), facilitator(s) and/or excipient(s) may be formulated with any of the thiol and/or disulfide compound(s). The kit may further comprise tools for mixing any of the kit components (compositions and the like) with other compositions (for example sunscreen compositions), receptacles and instructions for use.

The following aspects and embodiments refer to "a composition described herein"—it should be understood that compositions of this type are those compositions labelled as (i) and (ii) above.

The disclosure further provides a method of generating NO and/or at least vitamin D3 in the skin of a subject indeed thereof, said method comprising applying (or administering) a composition (or any one or more of the compounds) described herein to the skin of said subject; wherein upon exposure to a source of UV light (including the sun), the composition (or any one or more of the compounds) will generate NO and/or at least vitamin D3 in the skin of the subject.

The various NO generating (and/or Vitamin D(3)) generating compounds disclosed herein may be used or added to sunscreen compositions at any suitable concentration. For example, the compounds may be used or added at a (final) concentration of anywhere between about 0.1 µg to about 1000 µg and any value therebetween. For example the compounds may be used at a concentration of about 0.5 µg, 1 µg, 1.5 µg, 2 µg, 2.5 µg, 3 µg, 3.5 µg, 4 µg, 4.5 µg, 5 µg, 10 µg, 20 µg, 30 µg, 40 µg, 50 µg, 100 µg, 200 µg, 300 µg, 400 µg, 500 µg, 600 µg, 700 µg, 800 µg, 900 µg, 950 µg. One of skill will appreciate that the actual amount will depend, for example on a number of factors including the SPF rating of the composition, the make-up of the composition and the like.

As stated, vitamin D3 is synthesised in skin from 7-Dehydro Cholesterol (7-DHC) following exposure to UV-B. Sunscreen compositions block UV-B from impinging on the skin and inhibit the formation of Vitamin D3 from 7-DHC (see for example: J Reichrath. British Journal of Dermatology 2009 161 (Suppl. 3), pp 54-60). As such, continued use of sunscreen—while protective against some of the damaging effects of sun exposure, can lead to reduced NO/Vitamin D production. This is turn (particularly when combined with other conditions or factors which might affect NO/vitamin D production) may lead to the occurrence of disease and/or conditions associated with reduced, impaired and/or inhibited NO/vitamin D production. As such, the various sunscreen compositions provided by this disclosure may be used prophylactically to prevent or reduce the incidence of diseases associated with reduced, impaired or inhibited NO/vitamin D production. One of skill will appreciate that reduced vitamin D production is associated with, for example, MS, Alzheimer's, Cognitive impairment, asthma, cardiovascular disease, diabetes and cancer. Certain subjects, for example subjects with milk allergies and/or certain diets (for example Vegan diets) may be at further risk of vitamin D deficiency. Vitamin D is also important to the health of, for example bones, teeth and muscles (thus vitamin D deficiency can lead to diseases and/or conditions affecting teeth, bones and/or muscles—in other words the skeletomuscular structure of a subject). Of particular note are the conditions Rickets and osteomalacia which can be linked to vitamin D deficiency. As such, the compositions described herein may be used to help prevent (or treat) the occurrence or incidence of any of these diseases and/or conditions. In particular, the compositions described herein (including the sunscreen compositions) may be prescribed, administered to or applied to subjects (i) at risk of a vitamin D deficiency, (ii) predisposed or susceptible to a vitamin D deficiency and/or (iii) susceptible to and/or at risk of a disease and/or condition caused or contributed to by a vitamin D deficiency. As stated, subjects with allergies to certain vitamin D rich foods (for example, oily fish, milk, red meat, liver, egg yolks and fortified foods) or who have adopted specific vitamin D deficient diets (for example vegan diets) may particularly benefit from the compositions described herein.

Similarly, a nitric oxide deficiency can lead to diseases and/or conditions which affect, for example the cardiovascular system (nitric oxide being important in regulating circulation and dilation of blood vessels of all types (indeed the inventors have discovered that compositions (for example sunscreen formulations with nitric oxide generating components added) produce an increase in microcirculation flux in comparison to subjects that use prior art (non-supplemented sunscreen compositions)), the respiratory tract (again via effects on blood circulation), the musculo-skeletal system (via effects on muscle oxygenation and the like), cellular function (via effects on blood vessel development), the immune system, the nervous system, gastrointestinal tract and the urogenital system, (including matters connected with sexual health). As such, the compositions of this disclosure may be used on or applied/administered to subjects that are predisposed and/or at risk of developing diseases and/or conditions which might be caused or contributed to (or exacerbated by) a NO deficiency.

The compositions described herein are particularly useful as they augment NO/vitamin D production and counter the NO/vitamin D inhibiting effect of standard sunscreen compositions.

Thus, in one aspect, the disclosure provides a sunscreen composition of this disclosure (as described hereinabove) for use in augmenting NO/vitamin D(3) production in the skin of subject and/or for use in preventing the occurrence of diseases and/or conditions associated with reduced, impaired or inhibited NO/vitamin D(3) production. It should be noted that the phrase a "sunscreen composition disclosed herein" comprises sunscreen compositions that comprise, consist or consist essentially of, one or more compounds selected from the group consisting of:
  (1) a compound which upon exposure to sunlight (or the UV component thereof), generates NO or an intermediate or metabolite which can be used to generate NO in vivo;
  (2) a thiol compound (as described herein);
  (3) a disulphide (as described herein);
  (4) a compound which upon exposure to sunlight (or the UV component thereof), generates vitamin D or an intermediate or metabolite which can be used to generate active vitamin D in vivo; and
  (5) 7-dehydrocholesterol.

Based on the above disclosure, one of skill will appreciate that diseases and/or conditions associated with reduced, impaired or inhibited NO/vitamin D(3) production may occur in individuals using standard prior art sunscreens as these compositions impinge on the body's ability to generate NO/vitamin D(3) in response to exposure to sunlight (or at least a UV component thereof).

In another aspect, the invention provides a method of augmenting NO/vitamin D(3) production in the skin of subject and/or preventing the occurrence of diseases and/or conditions associated with reduced, impaired or inhibited NO/vitamin D(3) production, said method comprising administering (or applying) a sunscreen composition described herein to a subject in need thereof.

Note the term "subject" and/or "subject in need thereof" as used herein may embrace any subject (human or animal) about to expose themselves to the sun and in need of protection from the effects of sun exposure (sun burn and the like). These terms may also include any subject health or otherwise, needing to apply a sunscreen composition.

A further aspect of the disclosure provides methods of avoiding or countering the effect of sunscreen compositions on the formation or generation of NO/Vitamin D(3) in the skin of a subject, said method comprising supplementing a sunscreen composition with any of the compounds described herein including, for example, one or more compounds selected from the group consisting of:
  (1) a compound which upon exposure to sunlight (or the UV component thereof), generates NO or an intermediate or metabolite which can be used to generate NO in vivo;
  (2) a thiol compound (as described herein);
  (3) a disulphide (as described herein);
  (4) a compound which upon exposure to sunlight (or the UV component thereof), generates vitamin D or an intermediate or metabolite which can be used to generate active vitamin D in vivo; and
  (5) 7-dehydrocholesterol.

Note, compounds (4) and (5) may hereinafter be referred to as "vitamin D generating compounds".

Alternatively, the disclosure provides the use of any of the compounds described herein including, for example, one or more compounds selected from the group consisting of:
  (1) a compound which upon exposure to sunlight (or the UV component thereof), generates NO or an intermediate or metabolite which can be used to generate NO in vivo;
  (2) a thiol compound (as described herein);
  (3) a disulphide (as described herein);
  (4) a compound which upon exposure to sunlight (or the UV component thereof), generates vitamin D or an intermediate or metabolite which can be used to generate active vitamin D in vivo; and
  (5) 7-dehydrocholesterol.

There is also provided a method of augmenting NO/vitamin D3 production in a subject requiring to wear or use a sunscreen composition, said method comprising using, administering or applying a sunscreen composition as described herein.

A further aspect provides a method of providing a sunscreen composition which does not (substantially) inhibit NO/vitamin D production in a user and/or which facilitates, enhances, induces and/or stimulates a level of vitamin D/NO production in a user, said method comprising supplementing a sunscreen composition with one or more of the NO generating compounds described herein, including for example, one or more compounds selected from the group consisting of:

(1) a compound which upon exposure to sunlight (or the UV component thereof), generates NO or an intermediate or metabolite which can be used to generate NO in vivo;
(2) a thiol compound (as described herein);
(3) a disulphide (as described herein);
(4) a compound which upon exposure to sunlight (or the UV component thereof), generates vitamin D or an intermediate or metabolite which can be used to generate active vitamin D in vivo; and
(5) 7-dehydrocholesterol.

Also described is a composition (or any one or more of the compounds) described herein for use in generating NO and/or at least vitamin D3 in the skin of a subject in need thereof. It should be understood that a composition (or any one or more of the compounds) for use in this way may be applied or administered to the skin of said subject such that when the subject is exposed to a source of UV light (including the sun), the composition (or any one or more of the compounds) will generate NO and/or at least vitamin D3 in the skin of the subject. As stated, compositions of this type can be used prophylactically to avoid problems associated with reduced NO and/or vitamin D(3) production in subjects using (standard or prior art) sunscreen compositions.

Further, the disclosure relates to the use of a composition (or any one or more of the compounds) described herein for the manufacture of a medicament for generating NO and/or vitamin D3 in the skin of a subject in need thereof. A medicament of this type may be applied or administered to the skin of said subject such that when the subject is exposed to a source of UV light (including the sun), the composition (or any one or more of the compounds) will generate NO and/or at least a useful vitamin D precursor (for example vitamin D3) in the skin of the subject.

DETAILED DESCRIPTION

The present invention will now be described in detail by reference to the following figures which show:

FIG. 1: Generation of NO by skin samples following exposure to UV light

Figure 2:
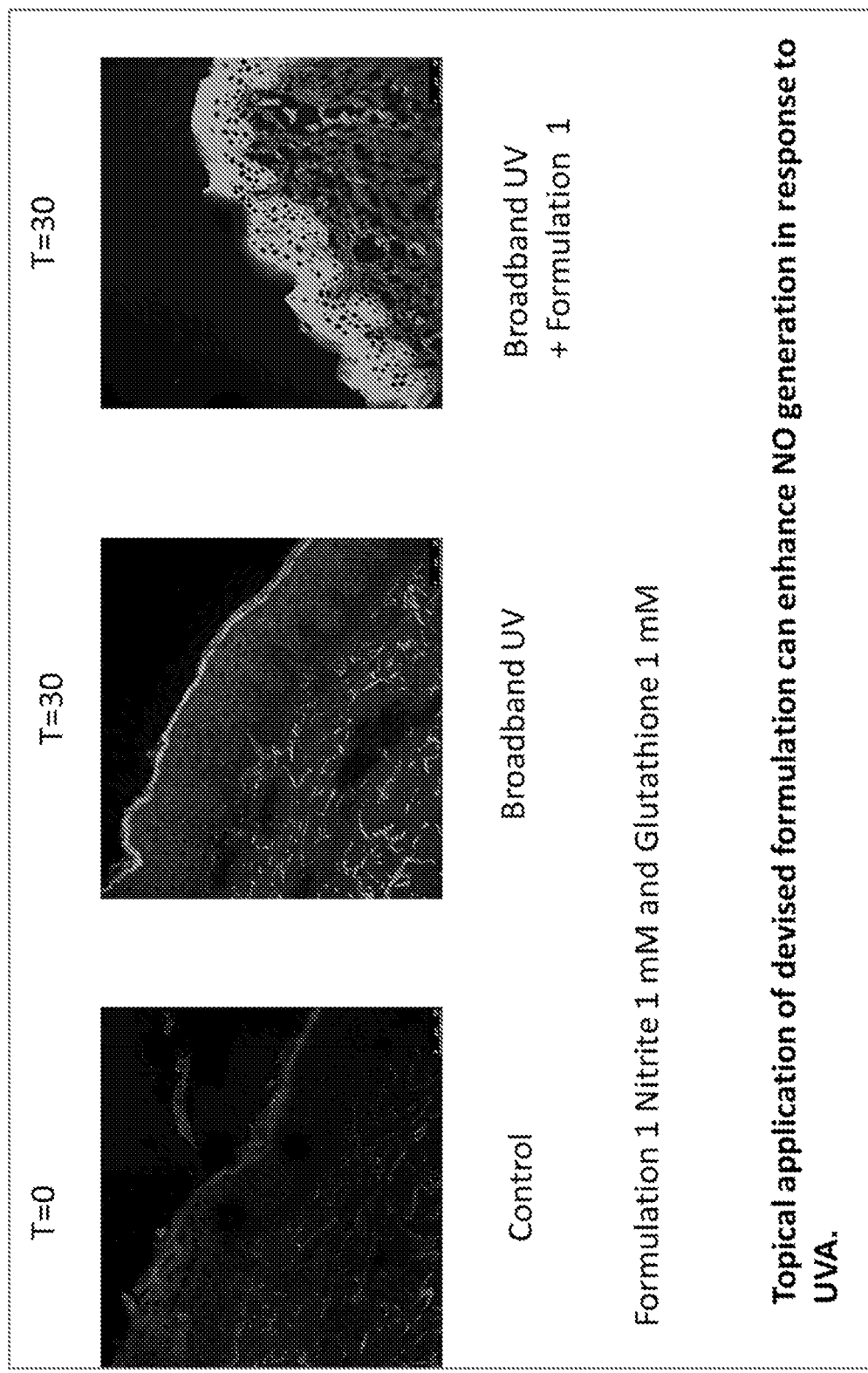

FIG. 2: Topical application of devised formulation can enhance NO generation in response to UVA.

Figure 3:
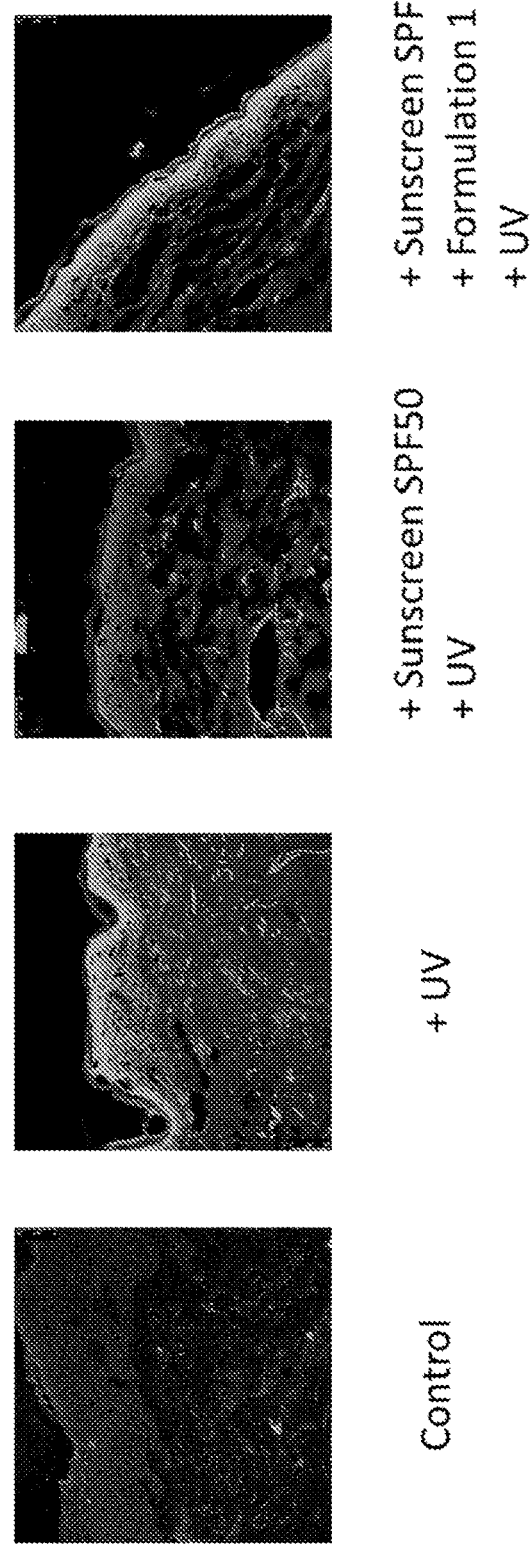

FIG. 3: Effects of UV on NO generation in the presence of SPF 50 sunscreen and SPF 50 sunscreen mixed with formulation 1.

Figure 4:
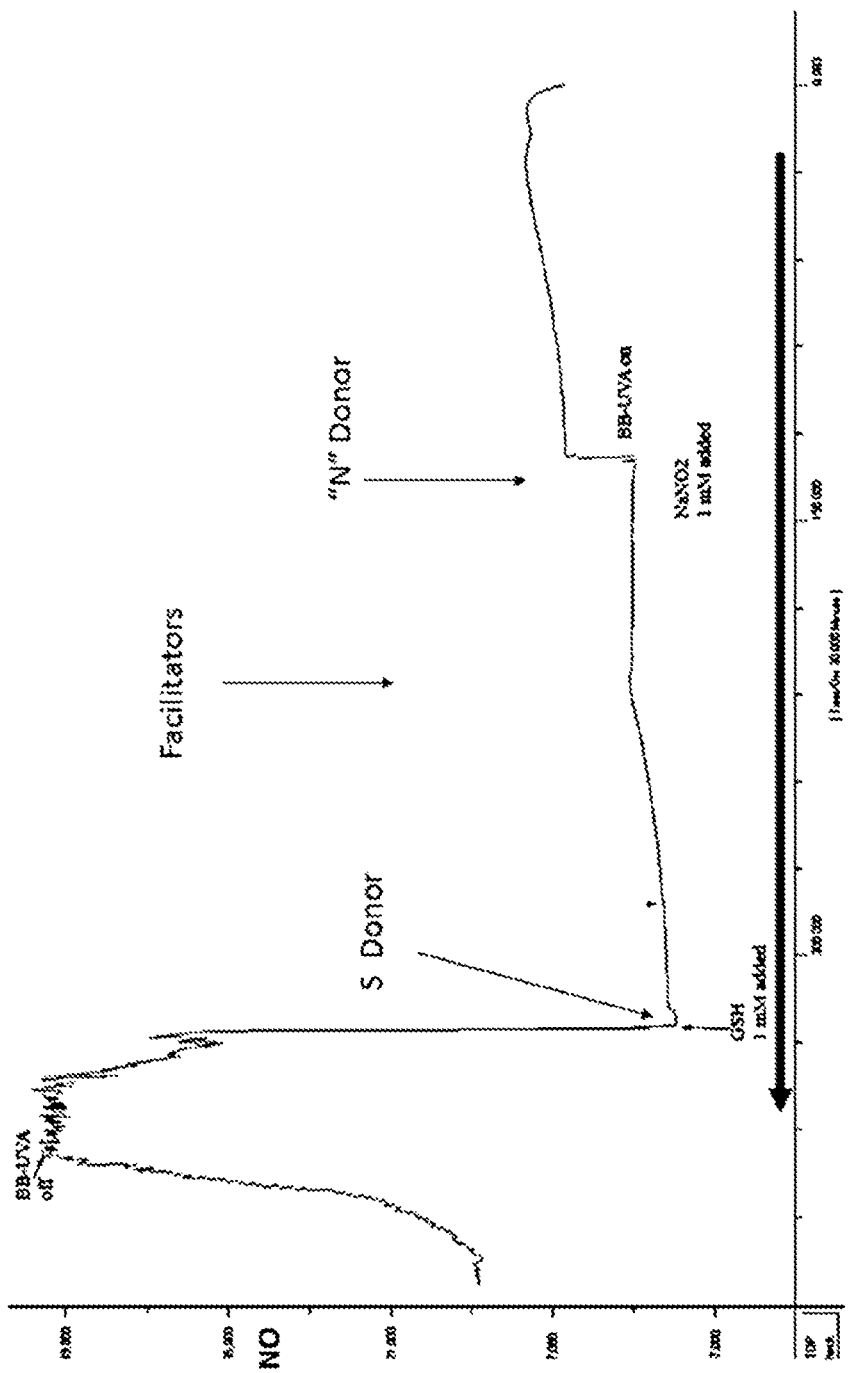

FIG. 4: Use of the Clarke electrode method in the determination of the effects of exogenous compounds on NO generation from skin homogenates in response to UVA.

Figure 5:
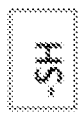
Figure 5:
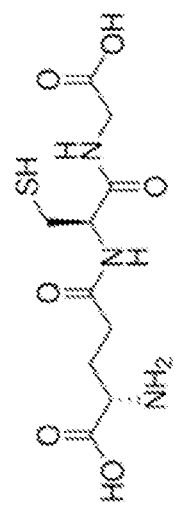
Figure 5:
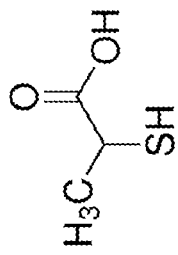
Figure 5:
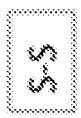
Figure 5:
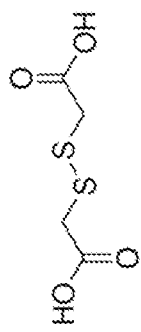
Figure 5:
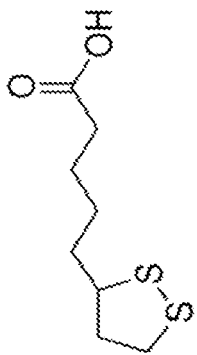
Figure 5:
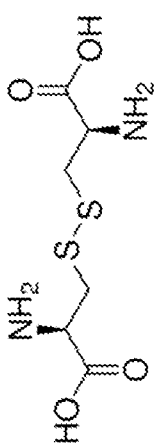

FIG. 5: Examples of the effects of "S" compounds on UV induced generation of NO from nitrite.

Figure 6:
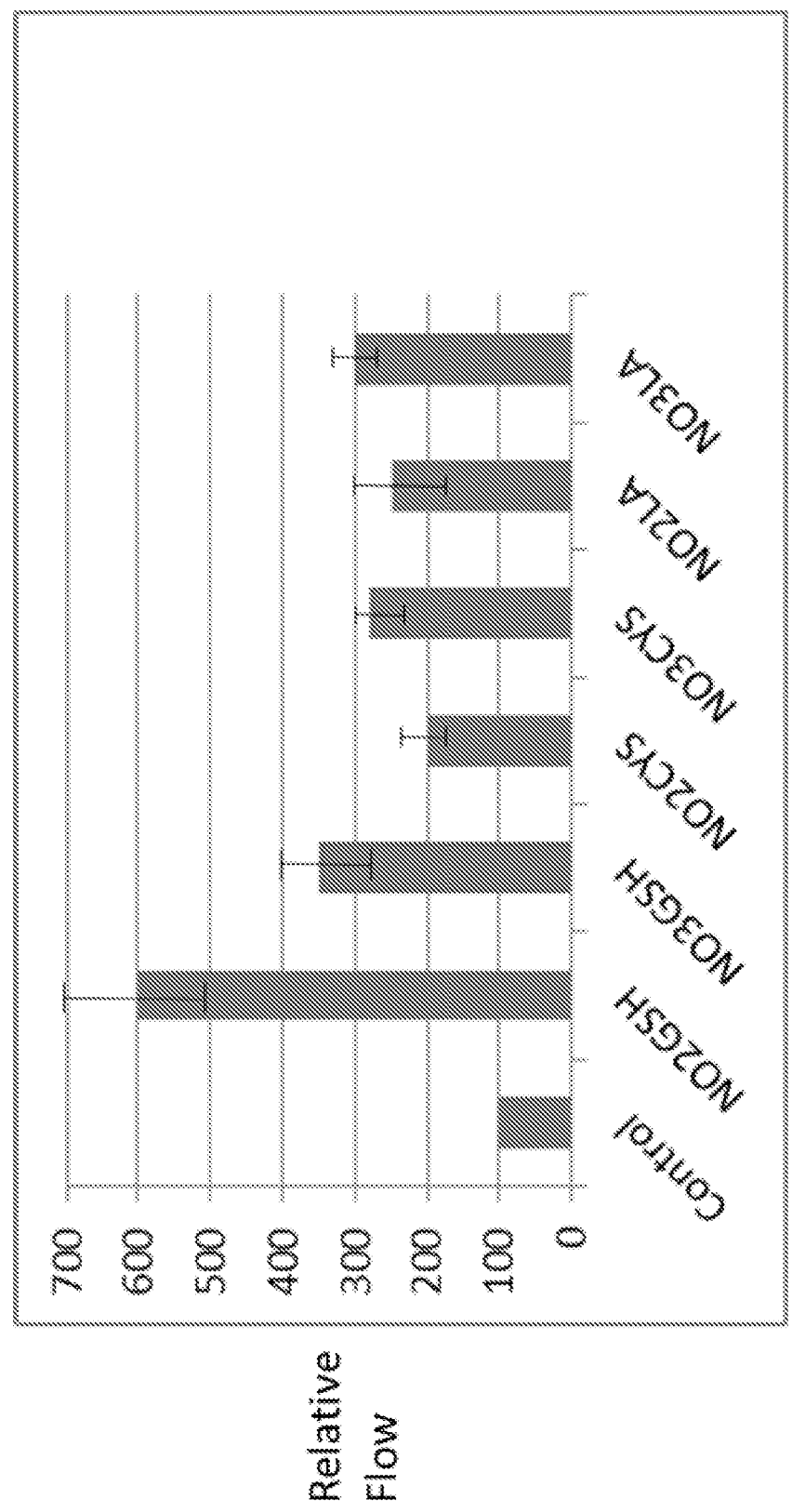

FIG. 6: The effects of organic sunscreens containing NO generating components on skin microcirculation in response to UV radiation.

Figure 7:
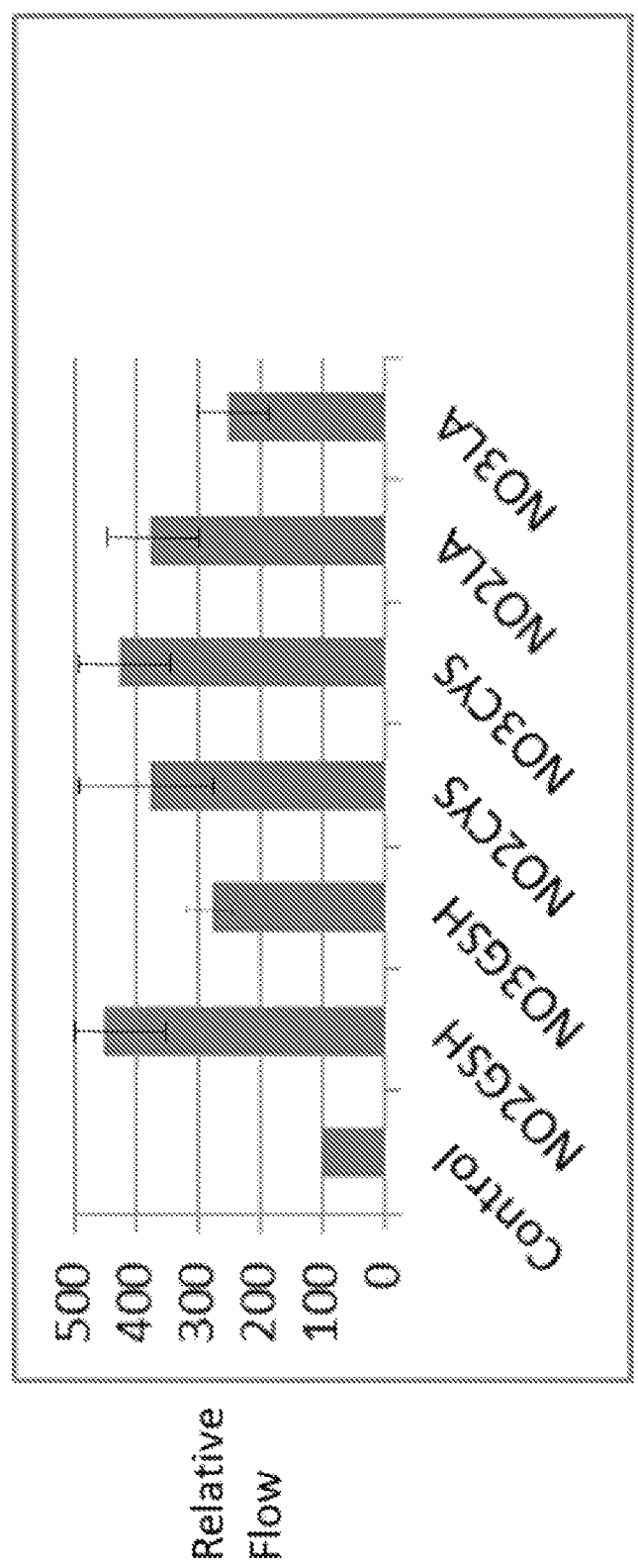

FIG. 7: The effects of physical sunscreens containing NO generating components on skin microcirculation in response to UV radiation.

Figure 8:
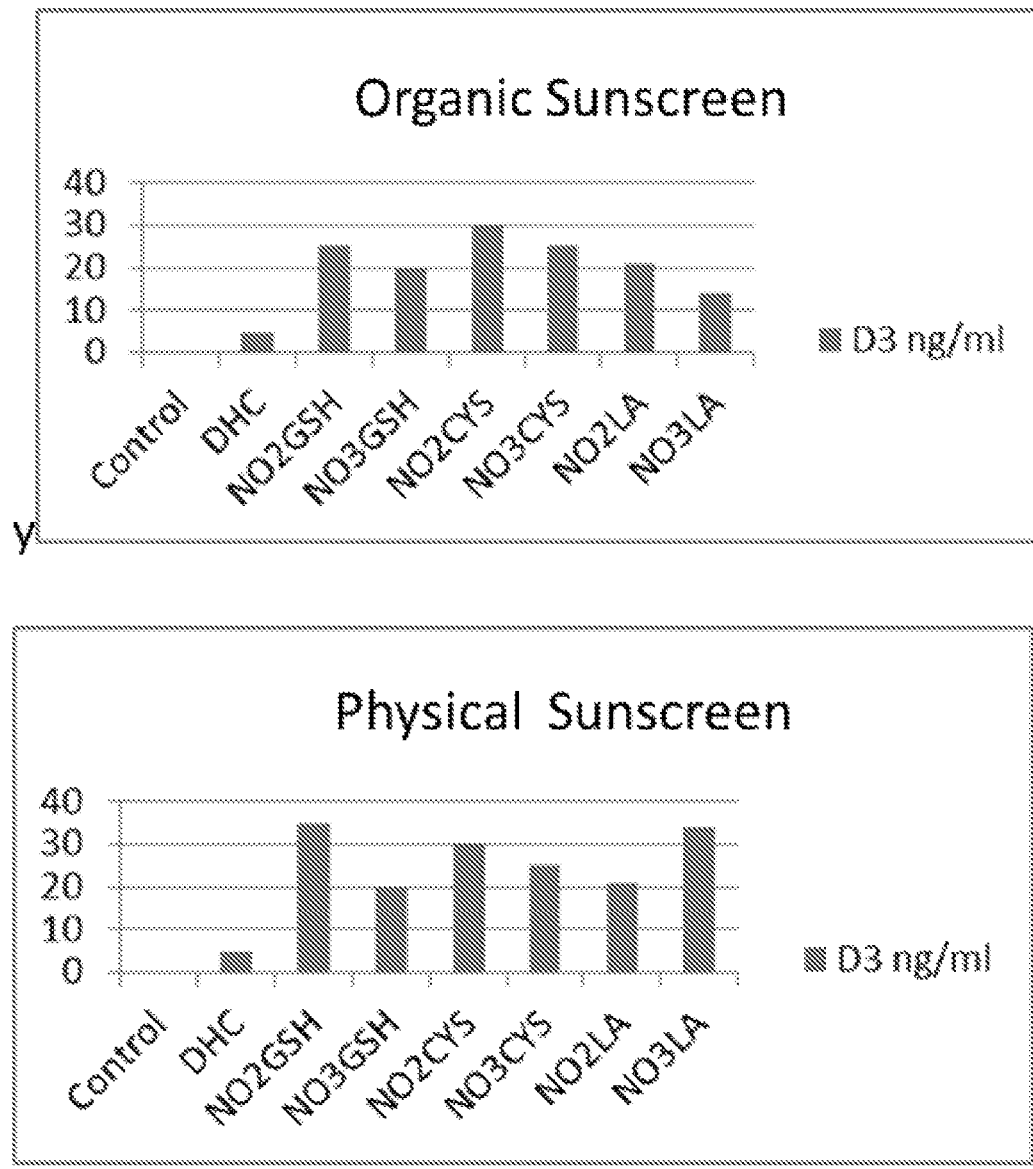

FIG. 8: The effects of NO generating components on the formation of Vitamin D3 from 7-DHC induced by UV light.

MATERIALS & METHODS

Histological Method for NO Determination in Skin.
Redundant skin from surgical procedures was snap frozen and microtomed to 5 mm sections. Sections were later incubated with 10 mM of the NO fluorochrome DAF-2DA for 1 hour at room temperature (Rodriguez et al., 2005). The applied DAF-2DA spontaneously crosses the plasma membrane into the skin cells and is cleaved by esterases to generate intracellular DAF-FM which cannot exit the cell. Skin sections were then irradiated with the light sources below for differing periods of time. On exposure to UV light NO generated oxidises the DAB-FM to a form a triazole product resulting in increased fluorescence.

A xenon arc lamp (Model 66021, Thermo Oriel) was used as light source

A monochromator (Model 77200, Thermo Oriel) with a xenon arc lamp (Model 66921, Thermo Oriel) was used to produce narrowband UV (280 -400 nm, half bandwidth 0.2 nm).

Broadband UVB 290-310 nm (300FS10-50 filter, L.O.T Oriel)

Broadband UVA 320-420 nm, (WG320+MUG2 filters, Schott)

Sections were then examined using a Leica SP5C spectral confocal laser scanning microscope (Wetzlar, Germany) and fluorescence intensities quantified using Image-Pro Plus (Media Cybernetics, Rockville, Md.).

For the investigation of the enhancing effects of exogenously applied formulations (as identified by the NO electrode method below) compounds were applied to the surface of the skin samples prior to irradiation. Typical results are shown in FIG. 2. Topical formulations enhancing NO generation increased NO production in the stratum corneum and epidermis.

For the investigation of the effects of sunscreen SPF factor 50 on UV radiation induced NO generation, commercially available sunscreen comprising both chemical and physical sunscreen barriers was applied to the surface of the skin prior to irradiation. Physical and chemical sunscreen ingredients were Zinc Oxide and Avobenzone. Exogenously added NO enhancing components were added directly to the sunscreen prior to application.

While sunscreen prevented the induction of NO production in skin in response to UV irradiation (FIG. 3) inclusion of NO enhancing formulation re-enabled the generation of NO in the presence of sunscreen.

Due to its small size and lipophilic behaviour, generated NO was transported from the stratum corneum, to the epidermis even in the presence of sunscreen.

Estimation of radiation transmitted through the sunscreen barrier in the presence and absence of NO enhancing formulations was made by measuring radiation transmission through a film of sunscreen on a microscope slide. Results shown in Table 1 show that the addition of NO enhancing formulation did not impair the radiation screening capacity of sunscreen.

Measurement of Vitamin D3 Production in Response to UV-B Irradiation in the Presence of Sunscreens.

Vitamin D3 (Cholecalciferol) was measured using an ELISA kit (AMS Biotechnology, 184 Millton Park, Abingdon, Oxford . OX14 4SE, UK) The ELISA is based on the competitive binding enzyme immunoassay technique. Skin samples were irradiated with UV-B radiation in the presence and absence of sunscreen products. In the presence of sunscreen UV-B irradiation reduced the production of Vitamin D3 in the skin. Sunscreen products supplemented with 7-dehydrocholesterol produced increased amounts of Vitamin D3 which was detected in the lower epidermal sections.

In Vitro Measurement of NO Generation as Determined by the NO Specific Clarke-Type Electrode Method.

Electrochemical sensors are widely used for the measurement of NO generation and Clark-type electrodes are most widely used as they are commercially available and easy to handle. The principle of these sensors is that NO diffuses through a gas-permeable membrane and a thin film of electrolyte, followed by oxidation on the working electrode. This oxidation creates a current that is proportional to the concentration of NO outside the membrane. The advantage of electrochemical NO sensors is the ability to directly detect NO concentration in solution or in biological samples with a low nanomolar detection limit. This makes NO electrodes an excellent tool for studying NO generation especially in biological samples.

Current theories of UV induced NO generation propose that UVA induced decomposition of nitrite (NO2-; equations 1-5 in Table 2) is self-limiting due to reaction with NO2. (equation 4 in Table 2). However it is proposed that in the presence of reduced thiols such as reduced glutathione, nitrosothiols are formed which then decompose on UVA challenge producing high levels of NO (equations 6-9 in Table 2). To date the only "thiol" reported to influence skin NO generation in response to UVA is reduced glutathione and cosmetically approved reagents have not been identified. Similarly, "N" sources identified as being involved in UVA induced NO generation are limited to nitrite and others have not been identified.

Likewise cosmetically acceptable facilitators and excipients to expedite NO formation in response to UVA have not been identified.

We used the Clarke electrode technique to investigate the mechanism of UVA light dependent NO generation in skin and cosmetically acceptable components which could facilitate augment the endogenous process. (FIG. 4).

Method

A 10% (g/mL) full thickness human skin homogenate in phosphate buffer was prepared using a glass/glass homogenizer. The homogenate was preheated at 56° C. for 1 hour to inactivate enzymatic generation of NO.

200 ul of homogenate was placed in a quartz cuvette in a thermostatically controlled environment and irradiated with broadband (320-400 nm) UVA radiation. Baseline signals were recorded.

Various sequential additions were made to the homogenate as indicated in FIG. 1 in order to identify (i) "N" donors able to contribute to the UV induced NO generation pathway.

(ii) Potential Thiol "S" participants in the UV induced NO generation pathway.

(iii) Facilitators and excipients able to enhance and sustain the NO generation pathway.

Results

Results are summarised in FIG. 5.

Unexpectedly both reduced (—SH) and oxidised (S—S) were effective in sustaining UV induced NO generation from a nitrite source.

In addition oxidised thiols (disulphide) such as lipoic acid and cystine were unexpectedly able to participate in sustained NO generation from nitrite in response to UVA radiation. However, not all disulphides sustained UV induced NO generation with Pantethine for example being ineffective. Oxidised Glutathione was effective, however.

We hypothesise that the capacity to participate in sustained NO generation in response to UV radiation is related to:

(i) the propensity of "S" containing compound to form the thiyl radical RS(dot) in response to UV irradiation. Once an RS (dot) is formed it will immediately trap NO (at trace level from nitrite or other "N" donor), forming a nitrosothiol.

(ii) In a subsequent step the nitrosothiol is then photolytically cleaved to release NO. The relative stability of the formed nitrosothiol and propensity of the thiol/disulfide to form RS(dot) will determine outcome.

Thiyl radicals are formed from one-electron oxidation of thiols. Thiol ionization, dissociation of S—H, is the most important single property of thiols governing reactivity. The S—H bond of thiols dissociates with pKa in the range ~7-10. However the response of Thiols to UV radiation will strongly depend on the chemical structures involved and the groups adjacent to the Thiol moiety.

Similarly the ability of disulphide bonds to form RS(dot) or dithiyl radical by the photolytic rupture of disulphide (S—S) bond will be highly dependent on the individual chemical structures involved.

The ability of a series of thiols RSH and disulfides RS—SR to generate RS(dot) and initiate sustained NO generation process will therefore strongly depend on the chemical structures involved.

Further use of the Clarke electrode method shown in FIG. 4 has identified other "N" donors that can participate in the UV radiation induced formation of NO (Table 3).

In addition factors and excipients which facilitate these reactions have also been identified (Table 3).

Tables

TABLE 1

| | Radiation Transmitted | |
|---|---|---|
| | BB-UVA (mW/cm$^2$) | UVA 290 nm (mW/cm$^2$) |
| Vehicle Control | 106.6 | 0.4 |
| Sunscreen alone (SPF50) | 11.5 | 0 |
| Sunscreen with Formulation 1 | 12.6 | 0 |

TABLE 2

| | |
|---|---|
| $NO_2^- + h\nu \rightarrow NO^\bullet + O^{\bullet-}$ | (1) |
| $O^{\bullet-} + H_2O \rightarrow OH^\bullet + OH^-$ | (2) |
| $NO_2^- + OH^\bullet \rightarrow NO_2^\bullet + OH^-$ | (3) |
| $NO_2^\bullet + NO^\bullet \rightarrow N_2O_3$ | (4) |
| $N_2O_3 + H_2O \rightarrow 2NO_2^- + 2H^+$ | (5) |
| $N_2O_3 + GS^- \rightarrow NO_2^- + GSNO$ | (6) |
| $GSNO + h\nu \rightarrow NO^\bullet + GS^\bullet$ | (7) |
| $NO_2^\bullet + GS^- \rightarrow NO_2^- + GS^\bullet$ | (8) |
| $NO^\bullet + GS^\bullet \rightarrow GSNO$ | (9) |

TABLE 3

| Active "S" donors | Active "Facilitators" | Active "N" donors |
|---|---|---|
| Glutathione | Ascorbate | Nitrite |
| Thiolactate | Ceramides | Nitrate |
| Dithioglycolate | Erucic Acid | 3-Nitropropionic acid |
| Lipoic acid (Oxidised) | Homocysteine | 9-Nitrooleate |
| Cystine | | 10-Nitrooleate |

EXAMPLE 2

To further examine the effects of enhancing formulations in sunscreens, on UV induced nitric oxide and vitamin D production, physical and chemical sunscreen formulations were formulated using the INCI listed compounds show in the tables below. For organic chemical sunscreens a generic oil in water formulation with known stability profile was selected for the base formulation using INCI ingredients shown in Table 4.

TABLE 4

INCI ingredients used in formulation of organic sunscreen base.

Aqua
Octocrylene
C12-15 alcohols benzoate
Butyl methoxydibenzoylmethane
Bis-ethylhexyloxyphenol methoxyphenyl triazine
Glycerin
Stearyl alcohol
Potassium cetyl phosphate
Coco-Caprylate
Nylon-12
Diethylhexyl butamido triazone
Phenoxyethanol
Polyacrylate-13
Polyisobutene
Disodium EDTA
Polysorbate 20

For physical sunscreen formulations a generic water-in-oil formulation containing both Titanium Dioxide and Zinc Oxide for sun protection was for the base formulation using INCI ingredients shown in Table 5.

TABLE 5

INCI ingredients used in formulation of physical sunscreen base.

Aqua
Isohexadecane
Propylheptyl Caprylate
Cyclopentasiloxane
Titanium Dioxide
Zinc Oxide
C12-15 alkyl benzoate
Triethylhexanoin
Polyglyceryl-3 Diisostearate
*Euphorbia Cerifera*
Glycerin
Magnesium Sulphate Heptahydrate
Aluminium Stearate
Alumina
Polyhydroxystearic acid
Phenoxyethanol
Ethyihexylglycerin Additions to the base formulations were made as follows.

Glutathione (GSH), cysteine (CYS), sodium nitrite (NO2) and sodium nitrate (NO3) were dissolved in a small amount of water and stirred into the finished bulk formulation after cooling to 30° C. 7-dehydrocholesterol (DHC) was dissolved in the hot oil phase just prior to emulsification. Lipoic acid (LA) was dissolved in a small amount of ethanol and stirred into the finished bulk after cooling below 30° C.

Effects of NO Generating Sunscreens on Skin Microcirculation in Response to UV Light.

Topical application of nitric oxide to the skin causes immediate vasodilation of the capillaries of the papillary plexus resulting in increased blood flow to the skin. This vasodilation results in an immediate transient localised erythema and dermal blood flow correlates directly with the concentration of NO delivered. This can be measured by Laser Doppler, a standard technique for the non-invasive blood flow monitoring and measurement of blood flow in the microcirculation (Seabra et al., British Journal of Dermatology 2004; 151: 977).

A laser Doppler perfusion monitor was used (Moor Instruments Ltd, Axminster, U.K.) with one satellite unit connected to the server allowed flux readings from two laser probes to be recorded simultaneously.

To measure the effects of sunscreen formulations on microcirculation control base sunscreen formulation was applied to one site on the forearm and sunscreen containing nitric oxide generating additives to the other site. A baseline recording was made in real time until readings had stabilised. In the absence of UV light no increase of blood flow flux was detected in response to the sunscreens. Recording was then paused, probes detached and the forearm area irradiated with broadband UV light for 5 minutes. Probes were then re-attached to the treated sites and recording of blood flow resumed. Cutaneous blood flow, measured as red blood cell flux, was used as an index of erythema.

Results are shown in FIGS. 6 and 7. Sunscreen formulations with nitric oxide generating components added produced an increase in flux in comparison to control sunscreen.

Enhancing Effects of NO Generating Components on the Formation of Vitamin D3 from 7-Dehydro Cholesterol.

Vitamin D3 is synthesised in skin from 7-Dehydro Cholesterol (7-DHC) following exposure to UV-B. Sunscreens block UV-B from impinging on the skin and inhibit the formation of Vitamin D3 from 7-DHC (J Reichrath. British Journal of Dermatology 2009 161 (Suppl. 3), pp 54-60). Since NO generation and 7-DHC conversion occur in the same cutaneous environment in response to sunlight and are both blocked by sunscreen use we investigated the effects of NO generating components on formation of Vitamin D3 from 7-DHC.

Sunscreen was applied to skin samples over an area of 10 $mm^2$ and irradiated with broadband UV-B (280-320 nm) radiation for 3 hours.

Skin samples were thoroughly wiped free of creams and 4 mm diameter punch biopsies on full thickness skin were taken and weighed. Skin specimens were then homogenized within 0.5 ml PBS buffer (pH7.2) and dispersed by vortexing and ultrasonication for 15 mins. 1 ml Hexane was added for lipid extraction. Samples were kept under 4 C overnight for Vitamin D3 extraction. Following centrifugation at 12000 rpm for 10 mins the upper Hexane phase was aspirated and dried under nitrogen. The nitrogen dried sample was re-suspended in aqueous buffer and Vitamin D3 quantified by ELISA (BioVision Vitamin D3 ELISA Cat # K4806-100).

Results are shown in FIG. 8. UV-B irradiation of skin alone did not result in Vitamin D3 production probably as a result of low endogenous levels of 7-DHC. Skin treated with organic or physical sunscreen supplemented with 7-DHC responded to UV-B irradiation by producing detectable levels of Vitamin D3. Unexpectedly, addition of NO generating components to 7-DHC supplemented sunscreens greatly enhanced the production of Vitamin D3 in response to UV irradiation.

The invention claimed is:

1. A sunscreen composition comprising one or more active ingredients that reduce the level of exposure to sunlight and/or UV components thereof, and further comprising:
   (I) (a) a thiol compound selected from the group consisting of: glutathione, cysteine, homocysteine, cysteamine, and thiolactate, and/or a disulfide selected from the group consisting of: dithioglycolate, lipoic acid (oxidised) and cystine; and
   (b) a NO-precursor compound selected from the group consisting of: nitrite-containing compounds, nitrate-containing compounds and nitro-containing organic compounds, wherein when the NO-precursor compound is a metal nitrate, the metal nitrate is selected from sodium or potassium nitrate; and
   (II) 7-dehydrocholesterol.

2. The composition of claim 1, wherein the thiol compound and/or disulfide comprises a compound capable of forming a photolytically cleavable nitrosothiol compound.

3. The composition of claim 1, wherein the NO-precursor compound is selected from the group consisting of:
- metal nitrites;
- (ii) sodium nitrite ($NaNO_2$);
- (iii) potassium nitrite;
- (iv) sodium nitrate;
- (v) potassium nitrate;
- (vi) carboxylic acid comprising a nitro (—$NO_2$) group;
- (vii) nitropropionic acid;
- (viii) nitrooleate;
- (ix) 3-nitropropionic acid;
- (x) 9-nitrooleate; and
- (xi) 10-nitrooleate.

4. A method of augmenting or stimulating NO/vitamin D3 production in a subject wearing or using a sunscreen composition, said method comprising applying or administering a sunscreen composition according to claim 1.

5. A composition comprising one or more active ingredients that reduce the level of exposure to sunlight and/or UV components thereof, and further comprising:

(I) (a) a thiol compound selected from the group consisting of: glutathione, cysteine, homocysteine, cysteamine, and thiolactate, and/or a disulfide selected from the group consisting of: dithioglycolate, lipoic acid (oxidised) and cystine; and (b) a NO-precursor compound selected from the group consisting of: nitrite-containing compounds; nitrate-containing compounds; and nitro-containing organic compounds, wherein when the NO-precursor is a metal nitrate, the metal nitrate is selected from sodium or potassium nitrate; and (II) 7-dehydrocholesterol;

wherein the composition is formulated for topical administration.

* * * * *

UNITED STATES PATENT AND TRADEMARK OFFICE
CERTIFICATE OF CORRECTION

PATENT NO. : 11,090,248 B2
APPLICATION NO. : 16/329945
DATED : August 17, 2021
INVENTOR(S) : Mike Finnen It is certified that error appears in the above-identified patent and that said Letters Patent is hereby corrected as shown below:

On the Title Page

(30) Foreign Application Priority Data: Please correct "1614961" to read -- 1614961.9 --

In the Specification

Column 2, Line 59: Please correct "$NO_2.$" to read -- $NO_2\cdot$ --

Column 5, Line 59: Please correct "(NO.)" to read -- (NO$\cdot$) --

Column 5, Line 62: Please correct "NO." to read -- NO$\cdot$ --

Column 5, Line 64: Please correct "NO." to read -- NO$\cdot$ --

Column 6, Line 3: Please correct "$NO_2.$" to read -- $NO_2\cdot$ --

Column 6, Line 8: Please correct "NO." to read -- NO$\cdot$ --

Column 6, Line 13: Please correct "NO." to read -- NO$\cdot$ --

Column 6, Line 15: Please correct "NO." to read -- NO$\cdot$ --

Column 6, Line 25: Please correct "NO." to read -- NO$\cdot$ --

Column 6, Line 28: Please correct "(RS.)" to read -- (RS$\cdot$) --

Column 6, Line 43: Please correct "(RS.)" to read -- (RS$\cdot$) --

Column 8, Line 6: Please correct "NO." to read -- NO$\cdot$ --

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*

Column 8, Line 26: Please correct "NO." to read -- NO· --

Column 9, Line 31: Please insert a paragraph break between "and" and "(5)"

Column 10, Line 31: Please correct "NO." to read -- NO· --

Column 10, Line 33: Please correct "NO." to read -- NO· --

In the Claims

Column 21, Line 6, Claim 3: Please correct "metal" to read -- (i) metal --